United States Patent [19]
Berg et al.

[11] 3,932,401
[45] Jan. 13, 1976

[54] MIXED ACRYLIC ACID/METHACRYLIC ACID ESTERS OF TRIS (HYDROXYALKYL) ISOCYANURATES

[75] Inventors: Carl John Berg, St. Paul; Edward John Deviny, Roseville, both of Minn.

[73] Assignee: Minnesota Mining and Manufacturing Company, St. Paul, Minn.

[22] Filed: Jan. 31, 1974

[21] Appl. No.: 438,207

[52] U.S. Cl............................ 260/248 NS; 96/115 P
[51] Int. Cl.²....................................... C07D 251/34
[58] Field of Search............................... 260/248 NS

[56] References Cited
UNITED STATES PATENTS
3,821,098   6/1974   Garratt et al. ...................... 260/248

*Primary Examiner*—John M. Ford
*Attorney, Agent, or Firm*—Alexander, Sell, Steldt & DeLaHunt

[57] ABSTRACT

The reaction product of a mixture of acrylic acid and methacrylic acid with tris (hydroxyalkyl) isocyanurates is found to have a reduced tendency to crystallize, making the reaction product especially useful in photopolymerizable compositions.

2 Claims, No Drawings

MIXED ACRYLIC ACID/METHACRYLIC ACID ESTERS OF TRIS (HYDROXYALKYL) ISOCYANURATES

BACKGROUND OF THE INVENTION

Reaction products of tris (hydroxyalkyl) isocyanurates, such as tris (2-hydroxyethyl) isocyanurate, and either acrylic or methacrylic acid, exhibit many of the properties needed by photopolymerizable monomers in a dry-film photoresist. For example, these reaction products may be dispersed into a film-forming polymeric binder material to provide a photosensitive layer that has the necessary balance between adhesion to, and removability from, a metal substrate that is to be processed using a photoresist. Further, these reaction products react rapidly upon exposure to an imagewise pattern of actinic radiation to provide an imagewise difference in the removability of the photosensitive layer from the metal substrate. And these reaction products contribute, together with the binder material, to the resistance and continued firm adhesion needed by the developed resist areas of the photosensitive layer during subsequent processing of the resist-covered metal substrate.

However, it has been found that dry-film photoresists that incorporate these monomers have inadequate storage life. After a period of storage of the photoresist, the monomers crystallize, whereupon the photosensitive layer of the photoresist loses the clarity and uniformity needed to achieve the desired rapid and full reaction upon imagewise exposure to actinic radiation, adhesion to substrate, and other desired properties. The result is that despite the unusually desirable combination of other useful properties exhibited by the described monomers, they have limited usefulness in photoresists because of their limited storage life.

SUMMARY OF THE INVENTION

The present invention provides a new class of monomers of the general type described above but which maintain their desired combination of properties throughout a long storage life. Briefly, the new class of monomers comprise the reaction product of 1. a tris (hydroxyalkyl) isocyanurate, represented by the formula,

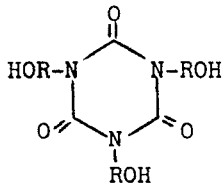

where R is alkylene of one to four carbon atoms; and
2. a mixture comprising acrylic acid and methacrylic acid, the weight-ratio of acrylic to methacrylic acid lying between 80:20 and 20:80, and sufficient acrylic and methacrylic acid being included in the reaction mixture to esterify at least 80 percent of the hydroxyl groups.

This new class of monomers is described herein as "chemically mixed" acrylic acid/methacrylic acid esters of tris (hydroxyalkyl) isocyanurates. (The term "chemically mixed" is used since acrylate and methacrylate groups can be formed during the reaction on the same molecule.) Although it has been found that a physical mixture of acrylates of tris (hydroxyalkyl) isocyanurate with methacrylates of tris (hydroxyalkyl) isocyanurate does not have the desired reduction in crystallization, the described chemically mixed esters do have the desired storage life. For example, dry-film photoresists using photopolymerizable monomers of the invention have been stored nearly a year without any tendency to crystallize.

DETAILED DESCRIPTION

As previously noted, the tris (hydroxyalkyl) isocyanurate ingredient in reaction products of the invention can be represented by the formula,

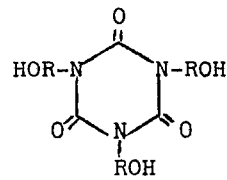

where R is alkylene of 1 to 4 carbon atoms. Preferably R is alkylene of 2 carbon atoms. These materials are prepared by known procedures (see U.S. Pat. Nos. 3,088,948, 3,121,082 and 3,249,607; and Z. N. Pazenko et al, UKR. KIHM. ZH. 30 (2), 195-8 (1964), for example); and at least one - tris (2-hydroxyethyl) isocyanurate - is available commercially as "THEIC" polyol from Allied Chemical Company.

Reaction of the described class of isocyanurates with a mixture of acrylic and methacrylic acid is conveniently conducted in benzene (to remove water of reaction), together with a catalyst such as p-toluene sulfonic acid and a polymerization inhibitor such as phenothiazine. A slight excess of acid may be used, and the reaction is continued until at least nearly the theoretical amount of water is collected. The reaction is generally conducted at a temperature in the range of 190°-215°F. Following completion of the reaction, the reaction product is typically washed several times with an alkaline solution, after which most of any remaining amount of benzene is removed.

Generally at least 80 percent of the hydroxyl groups on the isocyanurate are esterified and more preferably 90 percent or more are esterified. Any hydroxyl groups that are not esterified with acrylic or methacrylic acid may be subsequently allowed to react with some other compound, to achieve varied effects.

A variety of ratios of acrylic and methacrylic acid may be reacted with the isocyanurate. Improved properties are obtained when the weight-ratio of acrylic and methacrylic acid lies between 80:20 and 20:80, though the preferred range is from 70:30 to 50:50, and the most preferred product includes acrylate and methacrylate groups in a 60:40 ratio. At the outer limits of the described ranges, a greater tendency to crystallize has been noticed.

The monomers of this invention are generally dispersed in a polymeric binder material, together with a photoinitiator and other additives such as indicating dyes, adhesion promoters and pigments, to form a photopolymerizable composition. As noted above, one use for such a composition is as the photosensitive layer in a dry-film negative photoresist. In such a dry-film photoresist, the photopolymerizable composition is coated onto generally optically clear carrier film such as polyethylene terephthalate, and usually covered with a protective film such as polyethylene. Photopolymerizable compositions incorporating monomers of the invention can also be coated directly onto metal substrate to form a photoresist in situ.

The binder material in a photopolymerizable composition that incorporates monomers of the invention can be selected from a variety of polymeric film-forming materials. A number of useful binder materials are described in Celeste U.S. Pat. No. 3,469,982, one preferred class being polymers and copolymers based on various acrylates and methacrylates. Another preferred class of binder materials comprises the reaction products of styrene-maleic anhydride with dialkylamines to prepare half-amide products in which about one-third to two-thirds of the anhydride groups are reacted. Such modified polymers are described in an application of Berg, Ser. No. 438,206, filed the same day as this application, now U.S. Pat. 3,873,319. Generally between about 50 and 200 parts of the monomer of this invention, preferably 90 to 140 parts, are used with 100 parts of binder material.

The photoinitiator that is generally included in photopolymerizable compositions together with monomers of the invention can be any compound that will react upon exposure to actinic radiation to initiate polymerization of the monomer. Generally, the photoinitiator generates free radicals that cause addition-polymerization of the photopolymerizable monomer through reaction of the ethylenically unsaturated substituent ester groups on the isocyanurate ring. The photoinitiator should be thermally inactive at the elevated temperatures to which a photosensitive layer of a photoresist may be subjected during drying and heat-lamination steps; generally thermal stability in the range of about 250°–350°F. is satisfactory. Catalytic amounts of the photoinitiator are used, generally on the order of about 0.1 to 20 weight-percent, preferably 1–5 weight-percent, of the photopolymerizable monomer. A wide variety of photoinitiators are useful with photopolymerizable monomers of the invention, including substituted or unsubstituted anthraquinones and phenanthraquinones; vicinal ketaldonyl compounds, such as benzoin; and benzophenones.

Preferred initiators are vinyl-substituted halomethyl-s-triazines, such as 2-(4-methoxystyryl)-4,6-bis (trichloromethyl)-s-triazine, described in copending application Ser. No. 177,851, filed Sept. 3, 1971. These photoinitiators are preferred because they induce higher crosslinking rates for the photopolymerizable monomers than do other photoinitiators; low concentrations of these photoinitiators can be used because of their effectiveness; they are less oxygen-inhibited than other photoinitiators; and they do not require the presence of sensitizing dyes.

The invention will be further illustrated by the following example. A ten-gallon, glass-lined kettle equipped with a Barrett trap for collecting and measuring water of reaction was charged with the following ingredients:

|  | Grams |
|---|---|
| Acrylic acid | 3564 (49.5 moles) |
| Methylacrylic acid | 2838 (33 moles) |
| Tris (2-hydroxylethyl)-isocyanurate ("THEIC" polyol from Allied Chemical Company) | 6525 (25 moles) |
| P-toluenesulfonic acid | 545 |
| Phenothiazine | 1.3 |

The batch was heated with stirring to 175°F. to insure solution, after which 3,340 grams of benzene was added to form an azeotrope with water of reaction and thus aid in removal of the water. The temperature was increased to 190°–200°F., and in 2 hours 10 minutes, 1220 grams or 90 percent of the theoretical water had been collected. At this point the kettle was cooled rapidly. When the batch was below 75°F., 7.6 liters each of benzene and heptane were added. The solution was then washed several times with alkaline solutions and deionized water. The organic phase was placed over molecular sieves after these washings and stored overnight in a cooler. The liquid was then filtered off into a 20-gallon glass kettle, one gram of phenothiazene added, and benzene removed by applying a vacuum of 20 inches and heat at 125°F. for 1 hour. The product was then drained into an epoxy-lined pail. There was obtained 18.6 pounds of product (76 percent of the amount theoretically obtainable from the ingredients).

Next, a five-gallon, epoxy-lined pail, equipped with an air-motor-driven mechanical stirrer, was charged with 4600 grams of methyl ethyl ketone. A sheet of clear polytetrafluoroethylene (Teflon), having one hole for the stirrer shaft and another 1-inch diameter hole for a plastic funnel, was placed over the top of the pail. Next, 3,310 grams of styrene-maleic anhydride copolymer having a molecular weight of about 1600 (SMA-1000 A resin from Arco) was introduced into the pail through the funnel over a period of several minutes with stirring. The copolymer dissolved completely in the solvent in 45 minutes at 30°C. Next, 1210 parts of di-n-hexylamine was added smoothly through the funnel over a period of one minute, during which time there was an exotherm form 30°C. to 47°C. The solution was left to cool to room temperature, and then 1608 grams of a 2-weight-percent solids solution of 1,5-bis(4-dimethylaminophenyl) pentadienone-3 indicating dye in tetrahydrofuran was added with stirring.

Next, 5,025 grams of the photopolymerizable monomer described above, which included 10.4 percent of benzene solvent, was rapidly mixed into the solution. Then 904 grams of a 10 percent-solids solution of benzotriazole in tetrahydrofuran; 36 grams of a fluorocarbon surfactant; 246 grams of a 15 weight-percent-solids solution of 2-(4-methoxystyryl)-4,6-bis(trichloromethyl)-s-triazine in tetrahydrofuran; and 565 grams of an 8 percent-solids dispersion of duPont's Monastrol Blue BT 417D non-flocculating blue pigment in methyl isobutyl ketone were added to the solution.

The complete mixture was then coated onto a 2-mil thick polyethylene terephthalate film by an extrusion knife, and dried at 70°C. for 7 minutes to produce a 1.7-mil thick dry photosensitive layer. Thereupon the coated film was wound into a roll, together with a 2-mil thick liner or cover film of polyethylene.

The resulting dry-film photoresist was then tested by first removing the cover film and laminating the photoresist, photosensitive layer down, to a copper-clad substrate by passing the photoresist and substrate through pressure rolls that were heated to over 130°F. and applied 15–30 pounds per square inch pressure. The photosensitive layer was then exposed (through the polyethylene terephthalate film) through a high-contrast photographic transparency of a printed circuit pattern including a series of 5-mil wide lines separated by 5-mil wide spaces by low-pressure ultraviolet mercury lamps ("Colight" Model M-218 exposure frame using GE H400A-33-1/T 16 400-watt, mercury-vapor lamp bulbs) for 90–180 seconds. Next the polyethylene terephthalate carrier film was removed and a one percent-solids solution of sodium carbonate in water was sprayed onto the laminate through a commercial spray developer for 1 minute, which removed the nonexposed areas of the photosensitive layer. The result was well-defined tough adherent dimensionally true image or resist areas.

Next, the laminate was immersed for 36 minutes in a potassium copper pyrophosphate solution heated to 50°C. The laminate was then rinsed and dried by rubbing with a paper towel. No change was apparent in the image or resist areas.

The resist areas were then removed by spraying the laminate with a one percent-solids solution of sodium hydroxide in water heated to 150°F. for 1–2 minutes.

These tests were repeated on samples of the photoresist of this example at several month intervals through a period of eight months with similar results. Resist patterns prepared as described above were also successfully subjected to etching operations using ferric chloride, acidic ammonium persulfate, and even strong hydrochloric acid solutions.

What is claimed is:

1. The non-crystalline reaction product of
    1. 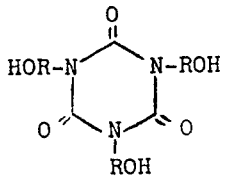

where R is alkylene of one to four carbon atoms, with
    2. a mixture comprising acrylic acid and methacrylic acid;

the weight-ratio of acrylic acid to methacrylic acid in the reaction mixture being between about 80:20 and 20:80, and sufficient acrylic acid and methacrylic acid being included in the reaction mixture to esterify at least 80 percent of the hydroxyl groups on the isocyanurate ring.

2. The non-crystalline reaction product of
    1. 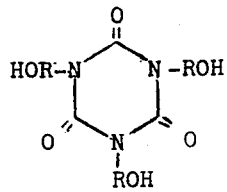

where R is ethylene, with
    2. a mixture comprising acrylic acid and methacrylic acid;

the weight-ratio of acrylic acid to methacrylic acid in the mixture being between 70:30 and 50:50, and sufficient acrylic acid and methacrylic acid being included in the reaction mixture to esterify at least 80 percent of the hydroxyl groups on the isocyanurate ring.

* * * * *